US00PP19052P3

(12) United States Plant Patent
Utecht

(10) Patent No.: US PP19,052 P3
(45) Date of Patent: Jul. 29, 2008

(54) ***PELARGONIUM* PLANT NAMED 'FISCODY'**

(50) Latin Name: *Pelargonium peltatum*
Varietal Denomination: Fiscody

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/528,939

(22) Filed: Sep. 28, 2006

(65) Prior Publication Data

US 2008/0127385 P1 May 29, 2008

(51) Int. Cl.
*A01H 5/00* (2006.01)

(52) U.S. Cl. ..... Plt./332
(58) Field of Classification Search ..... Plt./332
See application file for complete search history.

(56) References Cited

PUBLICATIONS

UPOV–ROM GTITM, Plant Variety Database 2007/02, GTI Jouve Retrieval Software, Citation for Pelargonium 'Fiscody', 2 pages.*

Floranova–Plant Breeders, [online], [retreived on Oct. 9, 2007]. Retreived from the Internet: <http://www.floranova-.co.uk/index.php>, 3 pages.*

* cited by examiner

*Primary Examiner*—Kent L Bell
*Assistant Examiner*—June Hwu
(74) *Attorney, Agent, or Firm*—Jondle & Associates, P.C.

(57) ABSTRACT

A new cultivar of *pelargonium* particularly characterized by having brilliant, deep-purple semi-double flowers, floriferous with small, compact umbels, medium-green foliage with weak zonation, a medium sized, well-branched, spreading to trailing plant habit and a mid-season flowering response, is disclosed.

2 Drawing Sheets

Genus and species: *Pelargonium peltatum.*
Variety denomination: 'Fiscody'.

BACKGROUND OF THE NEW PLANT

The present invention comprises a new and distinct cultivar of *pelargonium,* botanically known as *Pelargonium peltatum,* and hereinafter referred to by the cultivar name 'Fiscody'. The new cultivar is a product of a planned breeding program which had the objective of creating new varieties having bluish-purple flowers and fairly early flowering response. 'Fiscody' was discovered as a seedling resulting from the cross of the female parent 'I95-421-14' (unpatented), a proprietary *pelargonium* plant having pink single-type flowers, and the male parent 'Kleblue' (unpatented), a proprietary *pelargonium* plant having bluish-purple, double flowers.

The new cultivar was created in 2002 in Hillscheid, Germany and has been asexually reproduced repeatedly by vegetative cuttings in Galdar, Gran Canaria, Spain, and Hillscheid, Germany over a three-year period. It has been found to retain its distinctive characteristics through successive asexual propagations, 'Fiscody' reproduces true to type in successive generations of asexual reproduction.

Plant Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when grown under normal horticultural practices in Hillscheid, Germany.

1. Brilliant, deep-purple, semi-double flowers;
2. Floriferous with small, compact umbels;

3. Medium-green foliage with weak zonation;
4. A medium-sized, well-branched, spreading to trailing plant habit; and
5. A mid-season flowering response.

DESCRIPTION OF THE PHOTOGRAPHS

This new *pelargonium* plant is illustrated by the accompanying photographs which show overall plant habit including inflorescences, buds, and foliage of the plant; the colors shown are as true as can be reasonably obtained by conventional photographic procedures. The photographs are of three, 25-week-old, pinched plants grown from rooted cuttings, in a hanging basket taken in late summer 2005 in Hillscheid, Germany and grown under greenhouse and outdoor conditions which approximate those generally used in commercial practice.

DESCRIPTION OF THE NEW CULTIVAR

Figure 1:
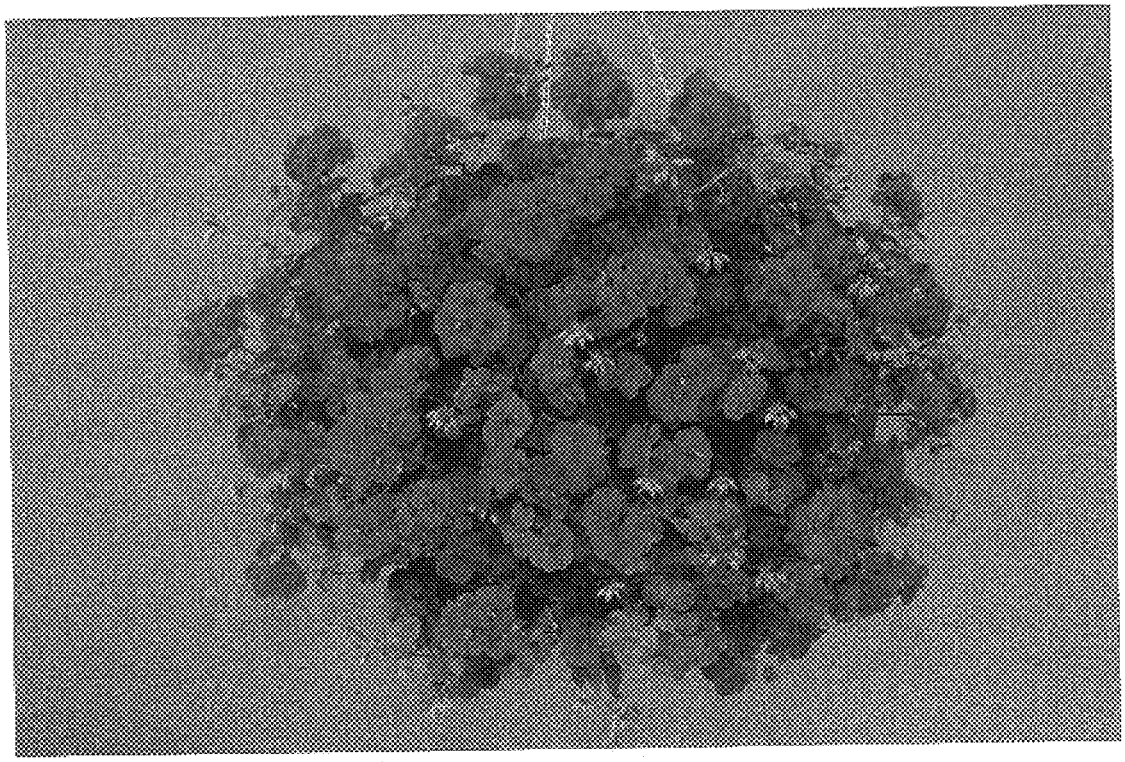
FIG. 1 shows the overall plant habit with blooms, buds and foliage
Figure 2:
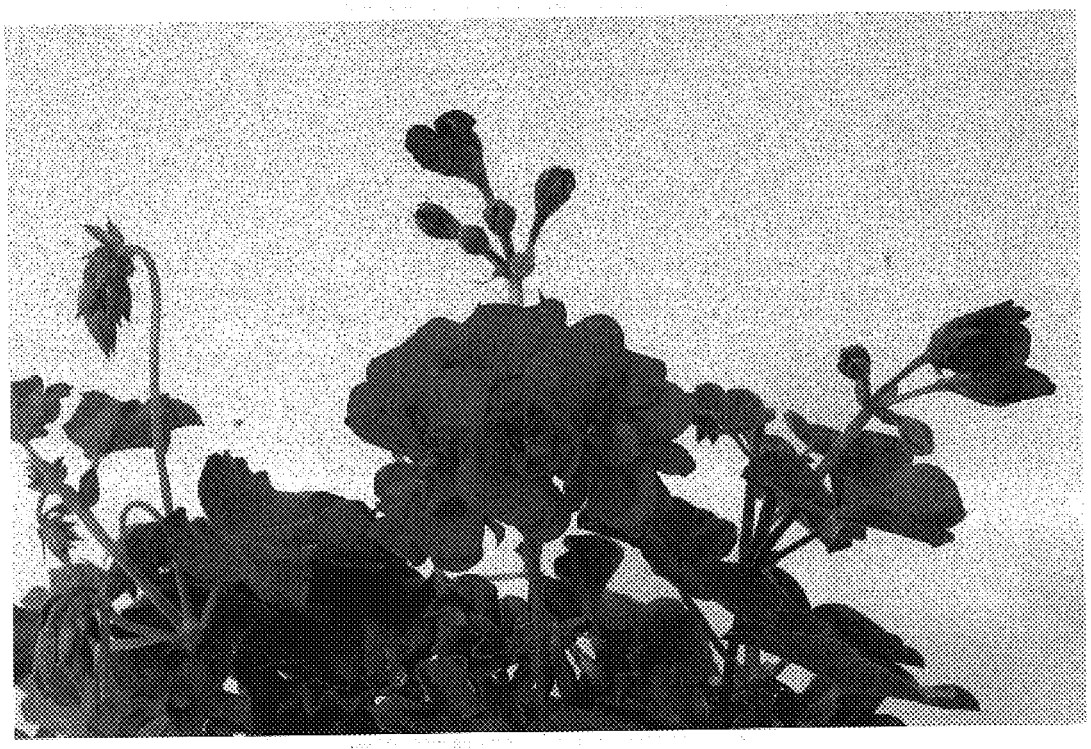
FIG. 2 shows a close-up view of an inflorescence.

The following detailed description sets forth the distinctive characteristics of 'Fiscody'. The data which define these characteristics were collected from asexual reproductions carried out in Hillscheid, Germany. The plant history was taken on 15-week-old, un-pinched plants in 12-cm pots in a greenhouse during late May 2005. Color readings were taken under natural light in late May from flowers grown in the greenhouse. Color references are primarily to the R.H.S. Colour Chart of The Royal Horticultural Society of London (R.H.S.) (2001).

DETAILED BOTANICAL DESCRIPTION

Classification:

*Family.*—Geraniaceae.

*Botanical.*—*Pelargonium peltatum* L'Héritier.

*Common name.*—Ivy geranium.

Parentage:

*Female parent.*'I95-421-14' a proprietary *pelargonium* plant having pink, single-type flowers (unpatented).

*Male parent.*—'Kleblue', a proprietary *pelargonium* plant having pale-bluish-purple, double flowers (unpatented).

Plant:

*Form.*—Shrub, self-branching, decumbent and trailing.

*Branching habit.*—9 to 12 branches per plant.

*Height* (*measured from base of the stem to the tips of the branches, excluding the inflorescence*).—14.3 cm.

*Width* (*plant diameter*).—31.7 cm.

*Time to produce a flowering plant.*—Plants had an average of 0.5 opened inflorescences at about 12 weeks after planting rooted cuttings in Hillscheid, Germany.

*Outdoor plant performance.*—Plants continuously flower; a count in late May of 2005 in Hillscheid, Germany produced about 3 to 5 inflorescences per plant; in late summer, plants about 30-weeks old, produced about 15 to 20 inflorescences per plant.

Leaves:

*Arrangement.*—Alternate, opposite at flowering branches.

*Immature leaf color.*—Grass-green. Upper surface: RHS 143A. Lower surface: RHS 143B.

*Mature leaf color.*—Upper surface: RHS 137D (medium-green). Lower surface: RHS 143A.

*Zonation color.*—RHS 166A (brown) with medium distinctness.

*Zonation diameter.*—Inner diameter of ring: 2.0 cm to 2.5 cm. Band or belt of zonation: 1.0 cm.

*Size.*—Length: 5.5 cm. Width: 8.9 cm.

*Shape.*—Ivy-shaped, with distinct lobes and with a gap between lowest lobes.

*Apex.*—Rounded, 5-lobed.

*Base.*—Cordate.

*Margin.*—Entire.

*Texture.*—Upper surface is leathery, smooth, and slightly glossy.

*Petioles.*—Color: RHS 143B (light-green). Length: 4.0 cm to 6.0 cm. Diameter: 0.25 cm. Texture: Very short pubescence.

Stems:

*Stem color.*—RHS 143B (green).

*Length.*—22.0 cm to 25.0 cm.

*Diameter.*—0.4 to 0.5 cm at midpoint.

*Internode length.*—0.5cm to 1.0 cm.

*Texture.*—Appear smooth, young stems with slight pubescence.

Inflorescence bud: (just before petals unfold).

*Shape.*—Elliptical.

*Size.*—Length: 1.5 cm. Width: 0.8 cm.

*Color of sepals.*—RHS 143C (light-green).

*Color of petals.*—RHS N74A.

Inflorescence:

*Inflorescence type.*—An umbel composed of 5 to 9 flowers.

*Umbel.*—Shape: Nearly semi-spherical, tight, relatively small. Diameter: 7.8 cm. Height (depth): 4.8 cm.

*Lastingness of umbel on the plant.*—About 14 to 16 days.

*Peduncle.*—Color: RHS 143C (light-green). Length: 12.7 cm. Diameter: 0.30 cm. Texture: With weak pubescence.

*Pedicel.*—Color: RHS 143B (grass-green). Anthocyanin: Absent. Length: 2.5 cm. Diameter: 0.15 cm. Texture: Dense pubescence.

Corolla:

*Shape of corolla.*—Wide open, often with a gap between upper petals and lower petals.

*Form.*—Semi-double to double.

*Diameter.*—5.0 cm.

*Depth.*—1.2 to 1.5 cm.

*Number of petals.*—10 to 13.

*Petaloids.*—Number: 0 to 2. Shape: Variable, shorter and narrower than the petals. Color: Outer (lower) surface: RHS N74B. Inner (upper) surface: RHS N74A to RHS N74B.

*Lastingness of individual flowers on plant.*—8 days at 18° C.

*Fragrance.*—None.

Petals:

*Shape.*—Upper petals: Spathulate. Lower petals: Obovate.

*Apex.*—Rounded.

*Base.*—Acute or Acuminate.

*Margin.*—Entire.

*Texture* (*for both the lower and upper surfaces*).—Smooth, slightly glossy.

*Upper petals.*—Length: 2.7 cm to 2.8 cm. Width: 1.7 cm to 1.8 cm. Color: Upper surface: RHS N74A (intense purple). Lower surface: RHS N74B (light purple), deep pink veins, RHS 67A towards the base. Markings: A small dark dot, RHS 59A, in the middle of the petal and a pair of fine, dark-veins, RHS 53A, from the base to the middle.

*Lower petals.*—Length: 2.3 cm to 2.4 cm. Width: 1.7 cm to 1.9 cm. Color: Upper surface: RHS N74A. Lower surface: RHS N74B.

*Markings.*—No distinct markings.

Sepals:

*Number.*—5.

*Color* (*both surfaces*).—RHS 143A to RHS 143B (grass-green).

*Anthocyanin.*—Absent.

*Length.*—1.0 cm to 1.2 cm.

*Width.*—Largest upper sepal: 0.5 cm. Other sepals: 0.3 cm.

*Shape.*—Lanceolate.

*Apex.*—Acute.

*Base.*—Fused.

*Margin.*—Entire.

*Texture.*—The outer (lower) surface has short pubescence and a few longer hairs, while the inner (upper) surface is glabrous.

Reproductive organs:

*Androecium.*—Number of anthers: 5 to 7. Filament length: 0.6 to 0.8 cm. Filament color: Mainly RHS 155D (white) to RHS 73A (purple-pink) at upper end. Pollen color: RHS 26A (yellow-orange). Pollen amount: Moderate.

*Gynoecium.*—Pistil: Number: 1. Length: 1.0 cm. Stigma color: RHS 71A (deep-purple). Stigma shape: 5 to 6 lobed. Style color: RHS 73D (pale-pink). Style length: 0.4 cm. Style shape: Filiform (filament-like) with the lobes of the stigma upright or at right angles.

Fruit and seed set: No seed set observed.

Disease and insect resistance: No particular resistance or susceptibility has been observed.

COMPARISON WITH PARENTAL AND COMMERCIAL CULTIVARS

'Fiscody' differs from the female parent 'I95-421-14' (unpatented) by having deep-purple, semi-double to double flowers, while 'I95-421-14' has pink, single-type flowers.

'Fiscody' differs from the male parent 'Kleblue' (unpatented) by having a slightly deeper flower color, flowers with fewer petals, stronger markings on upper petals and only 5 sepals compared to 'Kleblue'.

'Fiscody' differs from the commercial variety 'Fiscomedy' (U.S. Plant Pat. No. 9,394) by having fewer petals, smaller but more numerous inflorescences and an earlier flowering response than 'Fiscomedy'. In addition, 'Fiscody' has more upright directed branches and inflorescences, while 'Fiscomedy' has more creeping and trailing branches and inflorescences.

I claim:

1. A new and distinct cultivar of *pelargonium* plant as shown and described herein.

* * * * *